United States Patent [19]

Harvey

[11] Patent Number: 5,854,080

[45] Date of Patent: *Dec. 29, 1998

[54] PROCESS FOR SEPARATING TRITIATED WATER

[75] Inventor: James Travis Harvey, Naperville, Ill.

[73] Assignee: Eichrom Industries, Inc., Darien, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 883,288

[22] Filed: Jun. 26, 1997

Related U.S. Application Data

[63] Continuation of Ser. No. 483,846, Jun. 7, 1995, abandoned.

[51] Int. Cl.$^6$ .............................. B01D 15/04; G01N 1/34
[52] U.S. Cl. .................... 436/178; 210/662; 210/663; 210/682; 210/685; 436/39; 436/57; 436/161
[58] Field of Search .............................. 436/161, 57, 178, 436/144, 39; 210/661, 662, 663, 682, 683, 685, 690

[56] References Cited

U.S. PATENT DOCUMENTS

| | | | |
|---|---|---|---|
| 4,085,061 | 4/1978 | O'Brien | 210/682 |
| 4,138,329 | 2/1979 | Kita | 210/682 |
| 4,983,302 | 1/1991 | Balint et al. | 210/638 |
| 5,256,808 | 10/1993 | Alexandratos | 558/142 |
| 5,281,631 | 1/1994 | Horwitz et al. | 521/38 |

OTHER PUBLICATIONS

Baumann et al. *Anal. Chem. Nucl. Fuel Reprocess., Proc. ORNL Conf.*, 21st (1978).
Sundell et al., *Chem. Mater.*, 5:372–376 (1993).
Chang et al., *Chemical Abstracts*, 120:33 0597; *Taiden Heneng Yuekan*, 125:58–63 (1993).

*Primary Examiner*—Jan Ludlow
*Attorney, Agent, or Firm*—Welsh & Katz, Ltd.

[57] ABSTRACT

A process and apparatus for separating tritium from an aqueous solution that contains one or more additional dissolved radionuclides is disclosed. In accordance with the process the aqueous solution as a first liquid phase is contacted with each of three layers as a solid phase within a column. A first layer comprises particles having a plurality of pendent methylene diphosphonate groups. A second layer comprises strongly basic anion exchange particles, and a third layer comprises polymer particles free of ionically charged groups. The contact is maintained until a second liquid phase is formed that contains tritium as substantially the only radionuclide, and that second liquid phase is collected and can then be counted to determine the amount of tritium present. The column with its three layers constitutes the separation apparatus.

11 Claims, No Drawings

PROCESS FOR SEPARATING TRITIATED WATER

This is a continuation of application Ser. No. 08/483,846, filed Jun. 7, 1995, now abandoned.

DESCRIPTION

1. Technical Field

The invention is related to the separation of tritium as $T_2O$ or HTO from samples containing tritiated water and other elements, both radioactive and non-radioactive. More specifically, the invention relates to a process and an apparatus for the quantitative recovery of tritiated water in biological and environmental samples and that can also be used for monitoring tritium in nuclear power plant coolants as well as in weapons surveillance/monitoring programs.

2. Background Art

The use of nuclear technology, both in nuclear weapons production and in the generation of electricity by nuclear power, has led to health and safety concern by the public that has necessitated the monitoring of environmental and biological samples for tritium content. The most common type of biological sample analyzed for tritium is urine, whereas the most common type of environmental sample analyzed for tritium is water, i.e., tritiated water—HTO or $T_2O$.

Although the allowed dose of tritium to man is quite large when compared to other isotopes such as actinides or $^{90}Sr$, the amount of tritium produced during some power generation and weapons production activities is orders of magnitude larger than the amount of actinides or fission products produced. Consequently, there is a clear need for routine monitoring of certain biological and environmental samples for the presence of tritium.

There are a number of procedures for the determination of tritium as tritiated water. Almost all of these processes revolve around the separation of tritiated water from other elements (both radioactive and non-radioactive) by distillation techniques. As tritium is homogeneously distributed in the aqueous phase of an assayed sample, these procedures are all characterized by their collection of water vapor that has been driven from the sample. The distillation process is a laborious process that involves the set-up, use, and clean-up of a distillation apparatus for each sample. These apparati are bulky and typically require set-up in a laboratory fume hood. A typical cycle time for a single sample is two to three hours, most of which requires contact time by a laboratory technician. Consequently, the traditional tritium separation techniques are neither very economical nor practical.

In one atypical analysis Baumann et al. *Anal. Chem. Nucl. Fuel Reprocess., Proc. ORNL Conf.*, 21st (1978) reported a two-step tritium analysis process using ion exchange resins. In that procedure, the aqueous sample was first stirred batch-wise on a vortex mixer with equal equivalent amounts of ion exchange resins in the $OH^-$ and $H^+$ forms (Bio-Rad Laboratories, AG 1-X8 and AG 50-X8 resins respectively). The stirring lasted 20–40 minutes. The resulting aqueous slurry was then added to a column of a mixed bed resin (Rohm and Haas, Amberlite® MB-1), and the column was eluted with water. The radioactive decay within the eluate was measured by liquid scintillation counting.

Those authors reported that neither column ion exchange nor prolonged batch deionization was sufficient by itself to achieve the degree of decontamination required. Rather, only the batch exchange followed by a so-called final "polish" treatment sufficed to produce desired purity of the effluent HTO-containing water.

A mixed bed resin pretreatment followed by potassium permanganate double distillation of the resulting sample is a more recently reported method for tritiated water analysis. Chang et al., *Chemical Abstracts*, 120:33 0597; Taiden Heneng Yuekan, 125:58–63 (1993). This recently published method also requiring distillation suffers the same impairments of time and economy as to the traditional distillation processes.

Hence, a quick, accurate, and relatively inexpensive method for the quantitative analysis of tritium which may be found in biological and environmental samples is needed.

BRIEF SUMMARY OF THE INVENTION

The present invention contemplates a process and an apparatus for separating tritium as tritiated water from an aqueous sample.

One aspect of this invention thus contemplates a process for separating tritium (HTO or $T_2O$) from an aqueous solution that may contain one or more additional dissolved radionuclides. That process comprises the steps of:

(A) contacting a liquid phase that is an aqueous solution containing tritium as HTO or $T_2O$ and may contain one or more additional dissolved radionuclides present as inorganic anions or cations as well as radioactive or non-radioactive organic compounds with the solid phase contents of a column. Those solid phase contents comprise three water-insoluble layers of particulates.

A first of those layers comprises particles having a plurality of pendent methylene phosphonate groups such as those having pendent $CH(PO_3R_2)_2$ groups, wherein R is hydrogen, $Ca^{+2}$ or an alkali metal cation.

A second of those layers comprises particles that are strongly basic anion exchangers such as those having a plurality of pendent methylene tri-$C_1$–$C_3$ alkylammonium anion groups [—$CH_2N(R^2)_3{}^+X^-$, wherein $R^2$ is $C_1$–$C_3$ alkyl and $X^-$ is a hydroxide or halide anion].

A third of those layers comprises polymer particles that are free of ionically charged groups.

(B) The contact with each of those layers is maintained for a time sufficient for dissolved cations and anions present in said liquid phase to complex with phosphonate groups or exchange with the R groups of the pendent phosphonate-containing groups [$CH(PO_3R_2)_2$] and anions of pendent methylene $C_1$–$C_3$ trialkylammonium anion groups [—$CH_2N(R^2)_3{}^+X^-$] respectively, and for dissolved, organic compounds to bind to the polymer particles free of ionically charged groups to form a second liquid phase that contains tritium as substantially the only radionuclide.

(C) That second liquid phase is then collected.

An apparatus adapted for separating tritium as HTO or $T_2O$ from an aqueous solution containing tritium and may contain one or more additional dissolved radionuclides present in solution as inorganic anions or cations as well as radioactive or non-radioactive organic compounds constitutes another aspect of this invention. That apparatus comprises a cylindrical tube having an inlet means for an aqueous sample solution at one end and an outlet means for an aqueous eluate at the other end and having the above-discussed three layers of water-insoluble particles therebetween.

DETAILED DESCRIPTION OF THE INVENTION

The present invention contemplates an apparatus adapted for separating tritium as tritiated water from an aqueous solution containing tritium and that may contain one or more radioactive elements. A process for effecting that separation is also contemplated.

A contemplated process comprises three basic steps, i.e., contacting, maintenance and recovery, that are discussed in detail hereinbelow.

The tritium that is separated here is that element present as $T_2O$ or HTO in an aqueous solution of a sample to be assayed. The sample to be assayed can be from substantially any source, but is usually a biological sample such as urine, surface water or ground water or a sample from nuclear power coolant or weapons manufacture.

A sample used here may contain and usually does contain at least one additional radioactive element and often contains several such elements. Those other radioactive elements typically include polyvalent cations such as the transition metals, translanthanides and transactionides having valances of +3, +4, +5 and +6, or a radical such as the $UO_2^{+2}$ cation, but can also include monovalent species such as $Cs^{+1}$ and $I^{-1}$ and also divalent species such as $Sr^{+2}$ and $Ra^{+2}$.

An aqueous sample solution thus usually contains the additional radioactive element (radionuclide) as inorganic anions and/or cations. The additional radionuclide can also be present covalently or ionically bonded or complexed with an organic compound. Exemplary radioactive organic compounds, include $^{14}C$ compounds and radioactive mercury alkyls.

Non-radioactive organic compounds, particularly those that contain unsaturated bonds as are present in ketones and aromatic rings such as are found in proteinaceous materials containing tryptophan, phenylalanine and tyrosine, as well as nucleic acid bases, can quench fluorescence emissions used in scintillation counting, the preferred technique for assaying the amount of separated tritium. An aqueous sample may well contain such organic compounds, particularly where the sample is urine or from ground or surface water.

The aqueous sample constitutes one liquid phase in a contemplated recovery process. That liquid phase is contacted with the solid phase contents of a generally cylindrical column, such as a chromatography column, as is discussed in greater detail hereinafter. The solid phase within the column comprises three water-insoluble layers of particulate materials.

A first of those layers comprises particles having a plurality of pendent methylene diphosphonate groups; i.e., $CH(PO_3R_2)_2$ groups, wherein R is hydrogen, $Ca^{+2}$ or an alkali metal cation ($Li^{+1}$, $Na^{+1}$ and $K^{+1}$). A second of those layers comprises particles that are strongly basic anion exchangers such as those having a plurality of pendent methylene tri-$C_1$–$C_3$ alkylammonium anion groups; i.e., $—CH_2N(R^2)_3^+X^-$ groups, wherein $R^2$ is $C_1$–$C_3$ alkyl and $X^-$ is a hydroxide or halide anion. A third of those layers comprises particles that are free of ionically charged groups.

It is noted that it is not necessary or required that the particulate layers be ordered in the column as noted above. Any order can be used. However, it is preferred that each layer be serially contacted by the liquid phase in the order that each layer is recited. Thus, the first layer is preferably nearest to where the liquid phase enters the column and the third layer is preferably farthest from that place of entry and nearest to the place of egress for the liquid phase. The second layer is therefore preferably in the middle, between the other two layers.

It is also preferred that the layers remain separate and generally unmixed. Complete physical separation of the layers is not required, and some mixing can and does occur at the interface of one layer with the adjacent layer.

Each of the particle layers is described below.

The diphosphonate groups, trialkylammonium groups and aromatic sulfonate groups of the polymeric particles that constitute the various layers are referred to as being pendent. The word "pendent" is used to emphasize that the diphosphonate, trialkylammonium and sulfonate groups are not part of the copolymer backbone, but rather "hang" from that copolymer backbone via the intermediacy of another organic groups.

A contemplated particle of each of the three layers is insoluble in water as well as in organic solvents such as benzene, hexane, diethyl ether, acetone, ethyl acetate, dimethyl formamide (DMF), dimethyl sulfoxide (DMSO) and hexamethylphosphoramide (HMPA).

Turning now to first layer particles, those water-insoluble particles contain pendent methylene diphosphonate groups such as those that have the formula $CH(PO_3R_2)_2$, wherein R is hydrogen (a proton), $Ca^{+2}$ or an alkali metal cation such as lithium, sodium or potassium. The pendent methylene diphosphonate groups of these particles can exchange and also bind to (complex) cations, with complexation usually predominating in strongly acidic conditions; i.e., 1M nitric acid, and exchange occurring at higher pH values. These materials are cation exchangers.

A contemplated particle can be prepared from a variety of monomers, and three particular copolymer particles are preferred.

A first of these materials is a tetrapolymer whose synthesis and properties are discussed in U.S. Pat. No. 5,281,631, whose disclosures are incorporated herein by reference. These particles are available from Eichrom Industries, Inc. of Darien, Ill. under the name DIPHONIX™ and are used illustratively herein. Use of DIPHONIX™ particles is particularly preferred.

DIPHONIX™ particles are prepared by the copolymerization of four groups of monomers. Vinylidene diphosphonic acid or the alkyl or aryl esters thereof constitute one monomer group. The second monomer group comprises acrylamide or styrene, whereas the third group comprises acrylonitrile, methyl acrylate and methyl methacrylate. The fourth group comprises a divinylic or trivinylic cross-linking agent such as divinylbenzene, trimethylolpropane trimethacrylate, trivinylbenzene, diethyleneglycol diacrylate and N,N'-methylene-bis-acrylamide. Divinylbenzene often contains ethyl vinyl benzene as an impurity whose presence does not impair the efficacy of the particles.

Thus, a tetrapolymer is prepared by copolymerizing one monomer from each of the above four monomer groups. The diphosphonate-containing monomer is usually copolymerized as a tetraalkyl or tetraaryl ester whose ester groups are hydrolyzed off after completion of the reaction. A preferred synthesis for this monomer is disclosed in U.S. Pat. No. 5,256,808, whose disclosures are also incorporated by reference.

Styrene is a particularly preferred monomer of the second group and acrylonitrile is a particularly preferred monomer of the third group. When styrene is a copolymerized monomer, it is particularly preferred to sulfonate the copolymer particle beads (particles) to provide a copolymer having pendent phenylsulfonate groups. Any sulfonating agent can be used. Use of chlorosulfonic acid as sulfonating agent with a one hour reaction time at room temperature provides complete sulfonation of the phenyl rings. Subsequent hydrolysis with sodium hydroxide converts the chlorosulfonic acid groups to the desired sulfonate groups. Such sulfonation provides particles with enhanced hydrophilicity and microporosity and also typically hydrolyzes some pendent nitrile and ester groups to form pendent carboxylate groups, as well as hydrolyzing the diphosphonate tetraalkyl esters.

A second type of first layer particle has its pendent $CH(PO_3R_2)_2$ groups added to a preformed water-insoluble copolymer by grafting; i.e., the pendent phosphonate groups are added after copolymer particle formation.

A contemplated particle comprises an insoluble cross-linked copolymer having grafted pendent groups of the formula

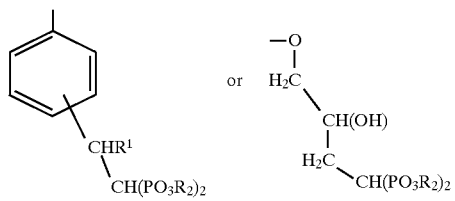

wherein R is selected from the group consisting of hydrogen, a $C_1$–$C_8$ alkyl group, a cation, and mixtures thereof; and $R^1$ is hydrogen or a $C_1$–$C_2$ alkyl group wherein phosphorus-containing pendent groups are present at 1.0 to about 10 mmol/g dry weight of said copolymer and the mmol/g values based on said polymer where $R^1$ is hydrogen. The particle also contains zero to about 5 mmol/g dry weight of pendent aromatic sulfonate groups.

A contemplated pendent methylene diphosphonate as first formed can contain a $C_1$–$C_8$ alkyl phosphonate ester. Exemplary $C_1$–$C_8$ alkyl groups of those esters and other $C_1$–$C_8$ alkyl groups noted herein include methyl, ethyl, propyl, isopropyl, butyl, t-butyl, pentyl, cyclopentyl, hexyl, cyclohexyl, 4-methylcyclopentyl, heptyl, octyl, cyclooctyl, 3-ethylcyclohexyl and the like, as are well known. An isopropyl group is a preferred R group. An $R^1$ $C_1$–$C_2$ alkyl group is a methyl or ethyl group.

After formation, the alkyl ester groups are hydrolyzed so that for use, R in the above formula is hydrogen (a proton), $Ca^{+2}$ ion or an alkali metal such as lithium, sodium and potassium ions.

As is the case of ion exchange resins generally, an R cation of a contemplated ion exchange resin can be changed at will from a first cation (including a proton) to a second cation by simply washing an aqueous composition of a resin first cation salt with an aqueous solution having an excess of the second cation. These procedures are well known and need not be discussed further.

The reacted monomers of a contemplated copolymer are quite varied. Exemplary reacted monomers are styrene, ethyl styrene, vinyltoluene, vinylxylene, acrylonitrile, a $C_1$–$C_8$ alkyl acrylate or methacrylate, a vinyl $C_1$–$C_8$ acyl ester, vinylchloride, a $C_1$–$C_8$ alkyl vinyl ether, a vinyl benzylhalide such as α-bromo- or α-fluoromethyl styrene and glycidyl acrylate or methacrylate.

A contemplated $C_1$–$C_8$ acyl group is an acyl form of one of the above $C_1$–$C_8$ alkyl groups, as appropriate. Some $C_1$–$C_8$ alkyl groups such as cyclohexyl and t-butyl do not have corresponding acyl groups as is well known.

A contemplated insoluble copolymer must contain at least 1.0 mmol/g dry polymer weight and preferably about 2.0 mmol/g of a reacted (copolymerized) vinylbenzyl halide or glycidyl acrylate or methacrylate or both so that the above amount of pendent phosphonate groups can be prepared. In addition, where a pendent aromatic sulfonate is present as is preferred, an appropriate amount of reacted aromatic monomer such as styrene, vinyl toluene or the like must also be present.

Preferably, the insoluble copolymer contains at least 2 mole percent reacted vinylbenzyl halide or glycidyl acrylate or methacrylate, with that percentage more preferably being about 10 to about 95 mole percent. One or more reacted monoethylenically unsaturated monomers as discussed before are present at about 2 to about 85 mole percent, with this monomer preferably including at least 5 mole percent of an above monoethylenically unsaturated aromatic monomer such as styrene, ethyl styrene, vinyl toluene (methyl styrene) and vinyl xylene.

A useful insoluble copolymer also includes a reacted cross-linking agent (cross-linker). Reacted cross-linking agents useful herein are also quite varied. Exemplary cross-linking agents useful herein are selected from the group consisting of divinylbenzene, trimethylolpropane triacrylate or trimethacrylate, erythritol tetraacrylate or tetramethacrylate, 3,4-dihydroxy-1,5-hexadiene and 2,4-dimethyl-1,5-hexadiene. Divinylbenzene is particularly preferred here.

The amount of reacted cross-linker is that amount sufficient to achieve the desired insolubility. Typically, at least 0.3 mole percent reacted cross-linker is present. The reacted cross-linking agent is preferably present at about 2 to about 20 mole percent.

These contemplated particles are the multi-step reaction product of a nucleophilic agent such as $CH[P(O)(OR)_2]^-$, which can be obtained by known methods, with a substrate. Thus, $CH_2[P(O)(OR)_2]$, where R is preferably an ester group, is first reacted with sodium or potassium metal, sodium hydride or organolithium compounds, e g., butyllithium, or any agent capable of generating a diphosphonate carbanion. The resulting carbanion is then reacted with a substrate that is a before-discussed insoluble cross-linked copolymer of one or more of vinyl aliphatic, acrylic, or aromatic compounds and a polyvinyl aliphatic, acrylic, or aromatic compound, e.g., divinylbenzene. That copolymer contains at least 2 mole percent of a reacted halogenated derivative of vinyl aromatic hydrocarbon such as vinylbenzyl chloride, or glycidyl ester group, preferably from 10 to 95 mole percent, about 2 to about 85 mole percent of monovinyl aromatic hydrocarbon such as styrene and at least 0.3 mole percent of polyvinyl aliphatic and/or aromatic cross-linker such as divinylbenzene, preferably 2–20 mole percent.

A suitable insoluble, cross-linked copolymer can be obtained by any well known method used in styrene or acrylate polymerization (e.g., suspension and emulsion polymerization) but the suspension method is preferred because the insoluble copolymer is formed as beads suitable for column separation processes and the diameter of the beads can be easily controlled. Such polymerization can be performed in the presence of no solvent; i.e., neat or without diluent as a bulk polymerization, to about 90 weight percent of inert solvent or diluent such as alcohols, aliphatic and aromatic hydrocarbons or any of their mixtures. The vinyl aromatic compounds can contain lower alkyl groups with 1 to 3 carbon atoms in addition to the vinyl group. Examples of such monomers are vinyltoluene and vinylxylene.

The next step in preparing contemplated particles is the substitution of a methylene diphosphonate group for the halogen atom in the halomethyl groups on the aromatic units (e.g., vinylbenzyl chloride) or, for example, the epoxide group in glycidyl acrylate or methacrylate. The copolymer containing such units is reacted with the carbanion CH[P(O)(OR)$_2$]$^-$. Halogen is thereby displaced from the halomethyl groups or epoxy groups are opened, and a polymeric resin containing pendent methylene diphosphonate groups is formed.

The reaction of tetraalkyl methylene diphosphonate (after it is converted into a carbanion with sodium or potassium metal, sodium hydride, butyllithium, etc.) with insoluble, cross-linked copolymer containing halomethyl, ester, or epoxy groups to graft the phosphorous-containing pendent groups can be carried out at temperatures between about −25° and about 250° C., preferably from about 100° to about 170° C. The reaction is preferably carried out while the copolymer is swollen by an organic solvent such as toluene, xylenes, ethylbenzene or mesitylene.

Thus, the reaction is preferably carried out by swelling a before-discussed insoluble cross-linked polymer in one of the aforementioned solvents for 0.1–2 hours at a temperature from ambient to the boiling point of the solvent, and subsequent addition of a 1- to 5-fold excess of tetraalkyl methylene diphosphonate carbanion in a small amount of the same solvent. Reaction is usually carried out by-refluxing a mixture at atmospheric pressure for one to 48 hours, preferably 10 to 24 hours.

The grafted copolymer product so prepared is recovered by separation from the liquid by filtering, centrifugation, decantation and the like. The grafted copolymer can be washed with organic solvents such as benzene, toluene or ethylbenzene to free the product of unreacted tetraalkyl methylene diphosphonate and dried.

The copolymer containing grafted methylene diphosphonate tetraalkyl ester groups in an amount corresponding to about 1.0 mmol/g of dry weight, preferably from 2 to 7 mmol/g of dry weight, is preferably reacted with a sulfonating agent such as chlorosulfonic acid, concentrated sulfuric acid or sulfur trioxide in order to introduce strongly acidic pendent aromatic sulfonic groups (shown below in pertinent part as before) into their structure. The presence of the sulfonate pendent groups confers the additional advantage of hydrophilicity to the particles and leads to a surprising enhancement in the rate of cation complexation without adversely affecting the observed selectivity.

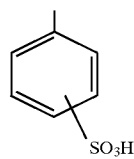

The reaction of the sulfonating agent with a grafted. copolymer containing methylene diphosphonate groups is usually carried out when the recovered resin product in ester form is swollen by a halohydrocarbon such as dichloromethane, ethylene dichloride, chloroform and 1,1,1-trichloroethane. The sulfonation reaction can be performed using 0.5 to 20.0 weight percent of chlorosulfonic acid in one of the mentioned halohydrocarbon solvent at temperatures ranging from about −25° to about 50° C., preferably at about 10° to about 30° C. The reaction is carried out by contacting resin preswollen for zero (unswollen) to about two hours with the above sulfation solution for 0.25 to 20 hours, preferably 0.5 to two hours.

After completion of the sulfonation reaction, the particles are separated from the liquid reaction medium by filtration, centrifugation, decantation, or the like. This final, second resin product is carefully washed with dioxane, water, 1M NaOH, water, 1M HCl and water, and then dried.

The sulfonation reaction and work-up in water also hydrolyzes the phosphonate C$_1$–C$_8$ alkyl ester groups. Where sulfonation is not carried out, hydrolysis of the phosphonate esters can be carried out by reaction with an acid such as concentrated hydrochloric acid at reflux.

These contemplated particles contain as functional groups both methylene diphosphonate and sulfonate groups, directly attached to carbon atoms of aromatic units or acrylate or methacrylate units in the polymer matrix. A contemplated resin displays high affinity towards a wide range of divalent, trivalent and multivalent cations over a wide range of pH values. At a pH value below 1, the resins are able to switch from an ion-exchange mechanism of cation removal to a bifunctional ion-exchange/coordination mechanism due to the coordination ability of the phosphoryl oxygens. The sulfonic acid groups then act to make the matrix more hydrophilic for rapid metal ion access; the methylene diphosphonate groups are thus responsible for the high selectivity.

A contemplated precursor insoluble copolymer can be prepared neat, in the absence of solvent or diluent by bulk polymerization techniques, or in the presence of a solvent or dispersing agent. A liquid solvent/dispersant is preferred here for use in a suspension polymerization so that the copolymer is prepared in the form of particles having a generally spherical shape; i.e., as beads, and a relatively narrow size distribution. Copolymer produced by bulk polymerization is typically broken to particles of irregular shape and a wide size distribution.

A contemplated copolymer and completed particle can have a size such that the particles pass through a sieve having a 4 millimeter (mm) opening and are retained on a sieve having an opening of about 0.004 mm. Particles that are sized to pass through a sieve screen with an opening of about 0.15 mm and be retained on a mesh of 0.004 mm are particularly useful for chromatographic separations. Larger sized particles are particularly useful for ion separations wherein the resin particles are filtered to effect a physical separation of one complexed polyvalent metal ion from one or more other mono- or polyvalent metal ions.

The preparation of ion-exchange/coordination particles containing both methylene diphosphonate and sulfonate groups on insoluble, cross-linked copolymers as herein described permits the production of materials having enhanced selectivity and improved kinetics of cation removal, especially in a low pH value range, than it has heretofore been obtained by the introduction of methylene diphosphonate or sulfonate groups alone.

The third type of first layer particles are copolymers described in Sundell et al., *Chem. Mater.*, 5:372–376 (1993) and Sundell et al., *Polym. Prep.*, 33:992 (1992) that are said to be useful as catalyst supports. These are terpolymers prepared by copolymerizing styrene, 1-(vinylphenyl) propane-2,2-bis(phosphonic acid) and divinylbenzene. In one reported synthesis, a microemulsion was prepared by the addition of water (0.26 g) to a styrene (23.52 mmol)/divinylbenzene (15.71 mmol) mixture containing bis(2-ethylhexyl)sulfosuccinate sodium salt (0.675 g). The above 1-(vinylphenyl)propane-2,2-bis(phosphonic acid) (1.4 mmol) was added portionwise to the microemulsion. The microemulsion was maintained at 30° C. until optically clear. Azobisisobutyronitrile (24 mg) was added, the reaction vessel was closed and polymerization was initiated by heating to a temperature of 60° C. for 12 hours. The resulting porous copolymer was then ground to form particles.

The particles of the second layer contain pendent methylene tri-C$_1$–C$_3$ alkylammonium anion groups; i.e., —CH$_2$N $(R^2)_3{}^+X^-$ groups wherein $R^2$ is $C_1$–$C_3$ alkyl, preferably methyl ($C_1$) and $X^-$ is hydroxide ($OH^-$) or a halide anion ($F^-$, $Cl^-$, $Br^-$ or $I^-$) with chloride ($Cl^-$) being preferred. Many useful materials are commercially available and are usually referred to as strongly basic anion exchangers or exchange resins.

Exemplary materials are sold under the trademarks AMBERLITE® IRA-900, -904, -400, -400OH, -402, -410, -420C, -458 and I 6766 and DOWEX® 1X2-100, 1X2-200, 1X2-400, 1X4-50, 1X4-100, 1X4-200, 1X4-400, 1X8-50, I 9880, I 0131, 1X8-100, 1X8-200, 1X8-400, 2X8-100, 2X8-200 and 2X8-400 from various suppliers such as Sigma Chemical Co., St. Louis, Mo. These materials typically have exchange capacities of about 1.8 to about 4.4 meq/g, are available in mesh sizes of 16–50 to 200–400 and typically contain about 2 to about 8 percent cross-links. Materials having a mesh size of about 100–400 and maximal exchange capacities are preferred. The particles sold as DOWEX® 1X8-200 are used illustratively herein and are particularly preferred.

These particles can also be readily synthesized by reaction of a copolymer having a reactive group such as a polymerized vinyl benzyl halide or glycidyl ester as described before with an appropriate tri-$C_1$–$C_3$ alkyl amine using well known reaction conditions. As is also well known, the anion present as obtained or prepared can be readily exchanged for a desired anion.

The cross-linked copolymer particles of the third layer are free of ionically charged groups; i.e., these particles have no acidic or basic groups that ionize in water. These particles thus differ from the first layer particles that contain pendent phosphonate and preferably also contain pendent phenylsulfonate groups that are anionic in water, and also the particles of the second layer that contain pendent trialkylammonium groups that are cationic in water.

Many particles useful in the third layer can also be purchased commercially. Exemplary materials available from Sigma Chemical Co. include those sold under the trademark AMBERLITE® XAD-2, XAD-4, XAD-7, XAD-16, XAD-1180, XAD-2000 and XAD-2010, those sold under the trademark DIAION™ HP 2MG, HP 20, HP 20ss, and 2P 20 ms, and those sold under the trademark AMBER-SORB™ 563, 575, 348F and 572. These materials are reported to be macroreticular resins of varying polarity that are typically prepared from acrylate or methacrylate esters or styrene with an appropriate cross-linker. These materials have typical wet mesh sizes of about 20–60, and pore sizes of about 20 Å to about 600 Å.

Another more preferred group of particles are those sold under the trademark AMBERCHROM® by Togo Haas Co. such as AMERCHROM® CG-161 and CG-71. The particles sold as AMBERCHROM® CG71 that are said to be cross-linked polymethacrylate ester materials have about a 100 to about 150 mesh size and pores of about 200 Å to about 300 Å are particularly preferred. These materials are smaller particle size versions of AMBERLITE® XAD materials.

Particles of each of the three before-described types are layered into a column such as a chromatography column, the barrel of a syringe or a disposable pipette. A frit, glass wool or other porous, non-adsorbing material as is well known is typically used at the bottom of a vertically held column to prevent loss of the particles or inhibition of eluate flow, and the three layers of particles are added thereabove. Another frit, glass wool or other porous, non-adsorbing material is typically added above the top-most layer to prevent disruption of the layers when the aqueous sample and eluant are added. Each layer is preferably added as a slurry in deionized or distilled water. The materials, packing and use of columns for ion exchange or complexation are well known by skilled workers and will not be gone into further.

The amount of each layer used with a given sample is dependent inter alia, upon the sample selected, its total concentration of ionic materials, the content of radioactive materials and the sample volume. A contemplated process and apparatus are particularly useful for sample volumes of about 1 to about 50 mL, or larger. Particles for the first two layers typically have minimal exchange capacities of about 1.2 meg/mL of water-swollen particles, and can readily accommodate tritium activities of about $10^2$ to about $10^8$ pCi/L as will be seen from the examples that follow.

Thus, a liquid phase that is an aqueous solution of the sample to be separated and usually assayed that contains tritium and can contain one or more additional dissolved radionuclides present as inorganic anions or cations, and which solution may further contain radioactive or non-radioactive organic compounds is contacted with the solid phase layered particles of the column.

That contact is maintained with each of the layers for a time period sufficient for the dissolved cations present in that liquid phase to be bound by (complex with) the diphosphonate groups or exchange with the R groups of the pendent diphosphonate [$CH(PO_3R_2)_2$] groups, and anions present to exchange with anions of the pendent —$CH_2N(R^2)_3{}^+X^-$ groups, respectively, and for dissolved organic compounds to bind to the particles that are free of ionically charged groups to form a second liquid phase that contains tritium as substantially the only radionuclide. In most instances, the second liquid phase that is present as the column eluate contains no other radioactive elements. However, some assays have shown that trace amounts of some elements such as $^{60}Co$ were not completely removed.

Exchange or complexation rates have not been measured with the layers of a contemplated column. However, it is believed that exchange or complexation is very rapid inasmuch as 25 mL aqueous samples passed through a 2.5 inch high column at a rate of 0.8 mL/minute exhibited no bleed-through of a multicomponent contaminant present in the sample at about the same activity as the tritium. Maintenance times are therefore minimal with each of the layers. This finding is contrary to the Report of Baumann et al., *Anal. Chem. Nucl. Fuel Reprocess., Proc. ORNL Conf.*, 21st (1978), 252–257 in which vortex mixing with anionic and cationic exchange resins for 20–40 minutes was insufficient to achieve desired exchange.

The second liquid phase is then collected, as by elution. Further material can sometimes be washed from the column with deionized or distilled water added at the top of the column. This collection step provides an aqueous solution of the separated tritium as HTO or $T_2O$. It is generally desired to determine the amount of tritium present in the collected solution and that can be determined by well known techniques for counting radioactive decay. Scintillation counting as is well known is a procedure of choice.

Thus, with knowledge of the original sample volume and that of the collected second liquid phase, as well as the radioactivity of that second liquid phase, one can readily ascertain the amount of tritium present in the original sample. Such radioactivity is usually reported in fractions of a Curie (Ci), one Ci being defined as $3.70 \times 10^{10}$ disintegrations/second.

As apparatus for separating tritium from an aqueous solution containing tritium as HTO or $T_2O$ that may also contain one or more additional dissolved radionuclides present in solution as inorganic anions or cations and radioactive or non-radioactive organic compounds is also contemplated. The apparatus comprises a cylindrical tube having an inlet means for an aqueous solution at one end and an outlet means for an aqueous eluate at the other end, and the before-described three layers of water-insoluble particles therebetween.

The cylindrical tube is the column discussed before and can be made of glass or a non-adsorbing plastic such as polyethylene or polypropylene, as is well known.

The inlet means is preferably at the top of a vertically-held tube and nearest to the first layer of particles, but need not be so placed so long as any entering aqueous solution can serially contact each of the before-described layers of particles. The inlet means is usually the open top of the tube that can have a reservoir area of widened diameter relative to the tube between the inlet means and the first layer of particles.

The outlet means is placed in the cylinder nearest the third particle layer such that an aqueous eluate must pass through each of the particle layers before encountering the outlet means. In usual practice, the outlet means is at the bottom of a vertically-held cylinder and has a means for restricting or stopping liquid flow through the cylinder such as a stopcock or pinch clamp on a flexible plastic tube. The outlet means is also typically of narrower diameter than is the cylindrical tube.

As noted previously, the names first, second and third layers are used principally for convenience in that the layers of particles need not be in a particular order in the column or when contacting the aqueous liquid. As also noted before, it is nonetheless preferred that the aqueous phase contact the solid phase particle layers in the order that those particle layers are named and described herein; i.e., first, second and then third. As a result; in preferred practice, the first layer containing pendent methylene diphosphonate groups is nearest the inlet means, the third layer containing particles free of ionic charges is nearest the outlet means and the second layer containing particles having pendent methylene trialkylammonium groups is between those two other layers of particles.

It is also preferred to have a frit, glass wool or other porous non-adsorbent material between the particle nearest the outlet means and the outlet means itself to prevent loss of the particles from the column in inhibition of flow. Similarly, such a porous material is preferably placed between the inlet means and nearest particles to inhibit disruption of the particle layer.

The following examples illustrate applications of the invention but are not to be construed as limiting its scope.

EXAMPLE 1
Tritium Separation and Counting

A tritium separation apparatus was prepared and used as follows. A disposable plastic cylindrical column was placed in a vertical position. The column had internal dimensions of about 6×0.7 cm, with a narrower diameter, tapering tip at the bottom and a chamber of about 3-times the column diameter (relative volume) at the top used for a reservoir and aqueous liquid phase inlet. A glass frit was placed in the bottom of the cylinder above the narrowed diametered portion. A slurry of AMBERCHROM® CG71 particles was added on top of the frit to a depth of about 0.5 inches (about 1.2 cm), followed by a slurry of DOWEX® 1X8-200 particles to a depth of about one inch (about 2.5 cm) and then a slurry of DIPHONIX™ particles to a depth of about one inch (about 2.5 cm). Each particle layer was gently added to the layer below to minimize disruption of the lower layer and mixing of the particles. A second frit was added above the top-most particle layer. The column so packed was then washed with about 10 mL of deionized water that was discarded after passage through the column, and the column had stopped dripping.

A 50 mL tube was then placed under the outlet. A measured 25 mL amount of the tritium-containing aqueous sample with or without other radioactive contaminants was added to the top of the column and permitted to flow therethrough by its own gravitational flow. The eluate liquid phase was collected in the 50 mL tube. A measured aliquot of the collected liquid was placed in a liquid scintillation vial, mixed with scintillation cocktail and counted in a Packard Liquid Scintillation counter.

The results of twenty-nine studies using separately prepared columns, each of which was prepared from an unused batch of particles are shown below in Table I. The identity of the components of the Contaminant composition and the activity of each of those components are shown in Table II thereafter.

TABLE I

Tritium Recovery Data

| Sample # | Volume mL | Tritium Added (dpm) | Tritium Found (dpm) | Percent Recovery | Contaminant Added (dpm) | Contaminant Found (dpm) |
|---|---|---|---|---|---|---|
| 1 | 15 | 5835 | 5660 | 97.00 | 0 | N/A |
| 2 | 15 | 5835 | 5590 | 95.80 | 0 | N/A |
| 3 | 15 | 5835 | 5666 | 97.10 | 0 | N/A |
| 4 | 15 | 5835 | 5602 | 96.00 | 0 | N/A |
| 5 | 25 | 1167 | 1096 | 93.90 | 0 | N/A |
| 6 | 25 | 1167 | 1081 | 92.60 | 1014 | N/A |
| 7 | 25 | 1167 | 1118 | 95.8 | 1014 | <MDA* |
| 8 | 25 | 0 | 0 | N/A | 0 | <MDA |
| 9 | 25 | 1167 | 1138 | 97.50 | 0 | N/A |
| 10 | 25 | 1167 | 1119 | 95.90 | 0 | N/A |
| 11 | 25 | 1167 | 1093 | 93.70 | 0 | N/A |
| 12 | 25 | 1167 | 1109 | 95.00 | 0 | N/A |
| 13 | 25 | 0 | 0 | N/A | 0 | N/A |
| 14 | 25 | 0 | 0 | N/A | 0 | N/A |
| 15GW | 25 | 1025 | 934 | 91.1 | 0 | N/A |
| 16GW | 25 | 1025 | 937 | 91.4 | 0 | N/A |
| 17GW | 25 | 1025 | 937 | 91.4 | 0 | N/A |
| 18GW | 25 | 1025 | 936 | 91.3 | 0 | N/A |
| 19GW | 25 | 1025 | 927 | 90.4 | 0 | N/A |
| 20SW | 25 | 242 | 220 | 90.8 | 1014 | <MDA |
| 21SW | 25 | 242 | 212 | 87.4 | 1014 | <MDA |
| 22SW | 25 | 242 | 225 | 92.8 | 1014 | <MDA |
| 23SW | 25 | 242 | 217 | 89.6 | 1014 | <MDA |
| 24SW | 25 | 242 | 218 | 89.7 | 0 | N/A |
| 25SW | 25 | 242 | 220 | 90.9 | 0 | N/A |
| 26 | 25 | 1213 | 1066 | 87.9 | 0 | N/A |
| 27 | 25 | 1213 | 1092 | 90.0 | 0 | N/A |
| 28 | 25 | 1213 | 1038 | 85.6 | 1014 | <MDA |
| 29 | 25 | 1213 | 1050 | 86.6 | 1014 | <MDA |

*less than minimum detectable activity
GW = ground water
SW = sea water
dpm = disintegrations/minute

TABLE II

Mixed-Contaminant Solution Activities

| Isotope | Activity (dpm) |
|---|---|
| Co-60 | 100 |
| Cs-137 | 187 |
| U-233 | 105 |
| Sr/Y-90 | 287 |
| Pb-210 | 235 |
| Th-230 | 100 |
| | 1014 total |

As is seen from the data of Table I, the tritium recoveries obtained using a contemplated separation process and apparatus were extremely good. Thus, more than 90 percent of the tritium added to a sample was recovered after separation in most cases. In addition, none of the added radionuclie contaminant was ever found in the column eluate.

EXAMPLE 2
Comparison of Column vs Distillation Separations

A series of studies was carried out under the direction of Dr. Daniel F. Cahil of Carolina Power & Lighting Company, New Hill, N.C. In these studies tritium was determined by the standard distillation method usually used in that facility and by a process of this invention. Results were compared for tritium activity found and time required to carry out the assays. The samples studied were from surface water, ground water and nuclear reactor cooling water. Columns used for these studies were prepared and used as described in Example 1. The results of this comparison are shown in Table III, below. Table IV thereafter provides the identities and activities of radionuclides present in the original reactor coolant water samples designated BWR and PWR.

TABLE III

| | H-3 Activity (pCi/L) | |
|---|---|---|
| Sample Type | Distillation Method* | Column Process* |
| Surface Water-40 | 4.48 ± 0.65E + 3 | 5.18 ± 0.67E + 3 |
| Surface Water-26 | 7.74 ± 0.70E + 3 | 8.07 ± 0.72E + 3 |
| Groundwater-16 | 3.37 ± 0.11E + 4 | 3.41 ± 0.11E + 4 |
| Groundwater-2C | 4,67 ± 0.12E + 4 | 4.48 ± 0.12E + 4 |
| BWR-RCS | 2.77 ± 0.01E + 6 | 2.74 ± 0.01E + 6 |
| BWR-RCS | 4.37 ± 0.0E + 8 | 4.10 ± 0.0E + 8 |

*$E + 3 = 10^3$; $E + 4 = 10^4$; $E + 6 = 10^6$; $E + 8 = 10^8$

TABLE IV

| Identity and Activity of Coolant Water Radionuclides ($\mu$ ci/mL) | | |
|---|---|---|
| | PWR* | BWR* |
| Cr-51 | 7.84E-5 | 5.38E-5 |
| Mn-54 | 1.40E-5 | 1.51E-4 |
| Co-58 | 1.28E-4 | 1.34E-4 |
| Fe-59 | 2.95E-4 | — |
| Co-60 | 1.06E-5 | 1.62E-4 |
| Sn-113 | 6.23E-6 | — |
| Nb-95 | 1.14E-4 | 3.14E-6 |
| Zr-95 | 5.98E-5 | — |
| I-131 | 3.84E-4 | — |
| Cs-134 | 3.04E-5 | — |
| Cs-137 | 3.58E-5 | — |
| La-140 | — | 4.18E-5 |
| Ce-144 | — | 5.48E-6 |

*$E - 4 = 10^{-4}$; $E - 5 = 10^{-5}$; $E - 6 = 10^{-6}$

The eluate from the BWR coolant water contained no detectable gamma activity. The eluate from the PWR coolant showed a trace of Co-60, which, as can be seen from Table III, had no effect on the tritium assay.

The time required to run ten samples by either method was three hours. However, the distillation apparatus required an additional two hours for clean-up.

As is seen from the data shown in Table III, the results obtained with either method were almost identical and were generally within the measured error for activity measured using the other procedure, thereby further validating the results obtained with the synthetic samples shown in Example 1.

EXAMPLE 3
Insoluble Copolymer Containing Grafted Tetraisopropyl Methylene diphosphonate Pendent Groups Tetraisopropyl methylene diphosphonate (346.5 g;. 1.0 mole) was dissolved in 1000 mL of dry toluene. To that solution, sodium metal (23.0 g; 1.0 mole) was added and the mixture was stirred overnight (about 18 hours) until sodium completely reacted.

Insoluble, cross-linked copolymer beads (100 g) were prepared by suspension polymerization of 67.47 weight percent vinylbenzyl chloride, 23.03 weight percent styrene, 5.0 weight percent divinylbenzene, and 0.5 weight percent benzoyl peroxide; ethylstyrenes were also present from the technical grade divinylbenzene. To introduce porosity, an equal amount of 1:1 (w/w) mixture of toluene and dodecane was added. The entire polymerization mixture was placed in a cylindrical reaction equipped with overhead stirrer, reflux condenser and thermometer, and was heated at 60° C. for one hour, 70° C. for one hour, 85° C. for two hours and finally at 95° C. for seven hours. Stirring speed was set to 280 rpm.

After polymerization was completed, the resulting cross-linked copolymer beads were separated on sieves, washed with hot water, water and acetone, then preswollen in toluene and extracted with this solvent for eight hours using Soxhlet apparatus, and then dried. The dried beads were placed in a three neck round bottom flask and preswollen with 500 ml of toluene for two hours at room temperature. A solution of sodium tetraisopropyl methylene diphosphonate was added to the flask and the entire mixture was reacted at reflux for 24 hours. After that time, the grafted resin was separated by filtration, washed with toluene, and dried. The beads contained 2.47 mmol of phosphorus/g of dry weight as determined by elemental analysis.

EXAMPLE 4
Resin with Pendent Aromatic Phosphonate and Aromatic Sulfonate Groups Resin (50 g) containing tetraisopropyl methylene diphosphonate groups as obtained in Example 3 was placed in an Erlenmeyer flask and preswollen with 300 mL of ethylene dichloride for one hour at room temperature. A solution of 50 mL chlorosulfonic acid in 150 mL of the same solvent was separately prepared, and then added to preswollen resin with continuous stirring. The chlorosulfonation reaction was carried out for one hour at room temperature. The sulfonated, diphosphonate resin was then separated from the reaction mixture by filtration, washed with dioxane, water, 1M NaOH, water, 1M HCl and with water, and then dried. The sulfonated, diphosphonate resin contained 2.26 mmol phosphorus/g of dry weight as determined by elemental analysis. Total acid capacity was 7.95 mmol/g of dry weight as obtained by NaOH titration.

EXAMPLE 5
Resin with Glycidyl Methacrylate-Pendent Tetraisopropyl Methylene Diphosphonate Groups Tetraisopropyl methylene diphosphonate (346.5 g; 1.0 mole) was dissolved in 1000 mL of dry toluene. To that solution, 40 g of 60 weight percent NaH suspension in mineral oil (24 g; 1.0 mole of pure sodium hydride) were added in portions, and the mixture was stirred until all NaH was reacted and a solution of sodium tetraisopropyl methylene diphosphonate was formed.

Insoluble, cross-linked copolymer beads (100 g) were obtained by suspension polymerization of 2.0 weight percent of 2-ethyl-(2-hydroxymethyl)-1,3 propanediol trimethacrylate, 97 weight percent of glycidyl methacrylate and 1.0 weight percent of benzoyl peroxide. The beads were placed in a three-neck round bottom flask and preswollen with 500 mL of toluene for one hour at room temperature.

The above solution of sodium tetraisopropyl methylene diphosphonate was added to the flask and the entire reaction mixture was heated at reflux for 24 hours. The resulting resin product was separated by filtration, washed with toluene, and dried. The dried resin contained 2.62 mmol of phosphorus/g of dry weight as determined by elemental analysis.

EXAMPLE 6
Resin with Glycidyl Methacrylate-Pendent Methylene Diphosphonic Acid Groups Resin beads (100 g) containing tetraisopropyl methylene diphosphonate groups (2.26 mmol of phosphorus/g of dry weight) as obtained in Example 5 were preswollen in acetone for 0.5 hour, washed with water and subsequently with 1M HCl. The resin beads were placed in a 1 L round bottom flask together with 600 mL of 5M hydrochloric acid solution. Hydrolysis was carried out by heating the mixture at reflux for two hours. After that time, resin beads were separated by filtration and conditioned with water, 1M NaOH, water, 1M HCl and water, and then dried. The total acid capacity for the hydrolyzed resin was 6.54 mmol/g of dry weight and phosphorus content was 3.22 mmol/g of dry weight as found by elemental analysis. Percentage of solid for this resin was 60.81 percent.

The foregoing description and the examples are intended as illustrative and are not to be taken as limiting. Still other variations within the spirit and scope of this invention are possible and will readily present themselves to those skilled in the art.

I claim:

1. A process for separating tritium as HTO or $T_2O$ from an aqueous solution that contains one or more additional dissolved radionuclides that comprises the steps of:
(A) serially contacting a liquid phase that is an aqueous solution containing tritium and one or more additional dissolved radionuclides present as inorganic anions or cations and may contain radioactive or non-radioactive organic compounds with each of three solid phase, water-insoluble particulate layers such that the liquid phase after each said contacting is contacted with another of said three layers until each said layer has been contacted, said three layers comprising:
(i) a first layer of particles having a plurality of pendent methylene diphosphonate cation exchange groups;
(ii) a second layer comprising strongly basic anion exchange particles; and
(iii) a third layer of polymer particles free of ionically charged groups;
(B) separately maintaining each of said contacts for a time sufficient for dissolved (i) cations to exchange or be bound by said methylene diphosphonate groups, (ii) anions present to be exchanged by said strongly basic anion exchange particles, or (iii) for organic compounds to bind to said polymer particles that are free of ionically charged groups, wherein each of said maintenance steps removes the respective cations, anions or organic compounds originally present in said liquid phase; and
(C) collecting the liquid phase after the third maintenance step to provide an aqueous solution containing HTO or $T_2O$.

2. The process according to claim 1 wherein said pendent methylene diphosphonate groups have the formula $CH(PO_3R_2)_2$, wherein R is hydrogen, $Ca^{+2}$ ion or an alkali metal cation.

3. The process according to claim 1 wherein said strongly basic anion exchange particles have pendent $—CH_2N(R^2)_3X^-$ groups as active exchange groups, wherein $R^2$ is $C_1–C_3$ alkyl and $X^-$ is a hydroxide or halide anion.

4. A process for separating tritium as HTO or $T_2O$ from an aqueous solution that contains one or more additional dissolved radionuclides that comprises the steps of:
(A) serially contacting a liquid phase that is an aqueous solution containing tritium and one or more additional dissolved radionuclides present as inorganic anions or cations and may contain radioactive or non-radioactive organic compounds with each of three solid phase, water-insoluble particulate layers such that the liquid phase after each said contacting is contacted with another of said three layers until each said layer has been contacted, said three layers comprising:
(i) a first layer of particles having a plurality of pendent $—CH(PO_3R_2)_2$ groups, wherein R is hydrogen, $Ca^{+2}$ or an alkali metal cation;
(ii) a second layer comprising particles having a plurality of pendent $—CH_2N(R^2)_3^+X^-$ groups, wherein $R^2$ is $C_1–C_3$ alkyl and $X^-$ is a hydroxide or halide anion, and
(iii) a third layer comprising polymer particles free of ionically charged groups;
(B) separately maintaining each of said contacts for a time sufficient for dissolved (i) cations to exchange or be bound by said pendent $—CH(PO_3R_2)_2$ groups, (ii) anions present to be exchanged by the anions of said pendent $—CH_2N(R^2)_3^+X^-$ groups, or (iii) for organic compounds to bind to said polymer particles that are free of ionically charged groups, wherein each of said maintenance steps removes the respective cations, anions or organic compounds originally present in said liquid phase; and
(C) collecting the liquid phase after the third maintenance step to provide an aqueous solution containing HTO or $T_2O$.

5. The process according to claim 4 wherein the particles of said first layer are selected from the group consisting of
(a) a cross-linked, water-insoluble tetrapolymer copolymerized from the monomers:
(i) vinylidene diphosphonic acid,
(ii) acrylamide or styrene,
(iii) acrylonitrile, methyl acrylate or methyl methacrylate, and
(iv) a divinylic or trivinylic cross-linking agent, said tetrapolymer further containing zero to about 100 mole percent sulfonated phenyl rings when monomer (ii) is styrene,
(b) a water-insoluble cross-linked copolymer having pendent groups of the formula

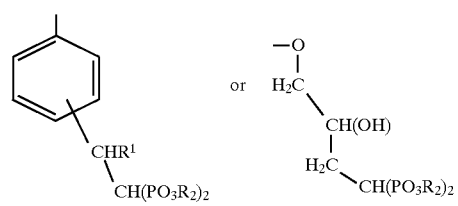

wherein R is hydrogen, $Ca^{+2}$ or an alkali metal cation, and
$R^1$ is hydrogen or a $C_1–C_2$ alkyl group, wherein phosphorous-containing pendent groups are present at 1.0 to about 10 mmol/g dry weight of said copolymer and the copolymer also contains zero to about 5 mmol/g dry weight of pendent aromatic sulfonate groups, the mmol/g values being based on the copolymer where $R^1$ is hydrogen; and (c) a water-insoluble terpolymer copolymerized from styrene, 1-(vinylphenyl)propane-2,2-bis(phosphonic acid) and divinylbenzene.

6. The process according to claim 4 wherein $R^2$ is methyl and $X^-$ is $Cl^-$.

7. The process according to claim 4 wherein the particles of said third layer are macroreticular resin particles.

8. A process for separating tritium as HTO or $T_2O$ from an aqueous solution that contains one or more additional dissolved radionuclides that comprises the steps of:

(A) serially contacting a liquid phase that is an aqueous solution containing tritium and one or more additional dissolved radionuclides present as inorganic anions or cations and may contain radioactive or non-radioactive organic compounds with each of three solid phase, water-insoluble particulate layers such that the liquid phase after each said contacting is contacted with another of said there layers until each said layer has been contacted, said three layers comprising:

(i) a first layer comprising particles that are selected from the group consisting of (a) a cross-linked, water-insoluble tetrapolymer copolymerized from the monomers:
(i) vinylidene diphosphonic acid
(ii) acrylamide or styrene,
(iii) acrylonitrile, methyl acrylate or methyl methacrylate, and
(iv) a divinylic or trivinylic cross-linking agent, said tetrapolymer further containing zero to about 100 mole percent sulfonated phenyl rings when monomer (ii) is styrene, (b) a water-insoluble cross-linked copolymer having grafted pendent groups of the formula

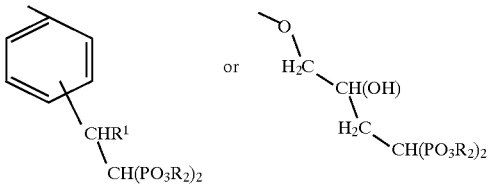

wherein R is hydrogen, $Ca^{+2}$ or an alkali metal cation, and $R^1$ is hydrogen or a $C_1$–$C_2$ alkyl group, wherein phosphorous-containing pendent groups are present at 1.0 to about 10 mmol/g dry weight of said copolymer and the copolymer also contains zero to about 5 mmol/g dry weight of pendant aromatic sulfonate groups, the mmol/g values being based on the copolymer where $R^1$ is hydrogen; and (c) a water-insoluble tetrapolymer copolymerized from styrene, 1-(vinylphenyl)propane-2,2-bis(phosphonic acid) and divinylbenzene;

(ii) a second layer comprising particles having a plurality of pendent —$CH_2N(CH_3)_3{}^+X^-$ wherein $X^-$ is a hydroxide or halide anion, and (iii) a third layer comprising macroreticular resin particles;

(B) separately maintaining each of said contacts for a time sufficient for dissolved (i) cations to exchange or be bound by said pendent —$CH(PO_3R_2)_2$ groups, (ii) anions present to be exchanged by said pendent —$CH_2N(CH_3)_3{}^+X^-$ groups, and (iii) for organic compounds to bind to said polymer.

9. The process according to claim 8 wherein said first layer is comprised of said tetrapolymer having styrene as monomer (ii).

10. The process according to claim 9 wherein said tetrapolymer has about 100 mole percent sulfonated phenyl rings.

11. The process according to claim 8 including the further step of determining the amount of radioactivity present in said collected second liquid phase.

* * * * *